US012576194B2

(12) United States Patent
Nagrath et al.

(10) Patent No.: US 12,576,194 B2
(45) Date of Patent: Mar. 17, 2026

(54) MICROFLUIDIC FLOW CONTROL USING DIRECT-CURRENT PERISTALTIC PUMP

(71) Applicant: THE REGENTS OF THE UNIVERSITY OF MICHIGAN, Ann Arbor, MI (US)

(72) Inventors: Sunitha Nagrath, Ann Arbor, MI (US); Kaylee J. Smith, Ann Arbor, MI (US); Kenn Oldham, Ann Arbor, MI (US); Jason Smyth, Ann Arbor, MI (US)

(73) Assignee: REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 1272 days.

(21) Appl. No.: 17/362,699

(22) Filed: Jun. 29, 2021

(65) Prior Publication Data

US 2022/0409790 A1 Dec. 29, 2022

(51) Int. Cl.
A61M 1/16 (2006.01)
A61M 1/26 (2006.01)
(Continued)

(52) U.S. Cl.
CPC .......... A61M 1/1603 (2014.02); A61M 1/267 (2014.02); B01L 3/50273 (2013.01);
(Continued)

(58) Field of Classification Search
CPC ............... F04B 49/065; B01L 3/50273; B01L 3/502761; A61M 60/279; A61M 60/113;
(Continued)

(56) References Cited

U.S. PATENT DOCUMENTS 3,788,471 A 1/1974 Buchmann et al.
3,791,767 A 2/1974 Shill
(Continued)

FOREIGN PATENT DOCUMENTS

EP 1910572 A2 4/2008
EP 2995953 A1 3/2016
(Continued)

OTHER PUBLICATIONS

Luc (Flow-rate Controlled Peristaltic Pump, Last Modified: Jul. 17, 2014, captured by Wayback Machine: Jun. 7, 2016, Retrieved: feb. 5, 2025, URL: https://web.archive.org/web/20160607025754/http://www.thepulsar.be/article/peristaltic-flow/) (Year: 2016).*
(Continued)

*Primary Examiner* — Ariana Zimbouski
(74) *Attorney, Agent, or Firm* — MARSHALL, GERSTEIN & BORUN LLP

(57) ABSTRACT

A peristaltic pump-based apparatus for capturing circulating tumor cells (CTCs) from blood is provided that includes a feedback control architecture that uses models of pump operation and measures of internal pressure fluctuations of the pump (e.g., in the form time-varying and/or position-dependent pressure oscillation data) to adjust pump operating characteristics that smooth pump operation, thereby improving viscosity and consistency of fluid flowing through the pump to a connected microfluidic capture device.

20 Claims, 9 Drawing Sheets

(51) Int. Cl.
  B01L 3/00 (2006.01)
  F04B 49/06 (2006.01)
(52) U.S. Cl.
  CPC ...... B01L 3/502761 (2013.01); F04B 49/065 (2013.01); A61M 2202/0407 (2013.01); A61M 2202/0409 (2013.01); A61M 2202/0411 (2013.01); A61M 2202/0443 (2013.01); A61M 2202/09 (2013.01); A61M 2202/097 (2013.01); A61M 2202/203 (2013.01); A61M 2202/206 (2013.01); A61M 2205/103 (2013.01); A61M 2205/3331 (2013.01); A61M 2205/3334 (2013.01); A61M 2209/088 (2013.01); B01L 2200/0668 (2013.01); B01L 2200/146 (2013.01); B01L 2400/0487 (2013.01)
(58) Field of Classification Search
  CPC ... A61M 1/3679; A61M 1/1603; A61M 1/362
  See application file for complete search history.

(56) References Cited

U.S. PATENT DOCUMENTS

| | | | |
|---|---|---|---|
| 5,284,470 A * | 2/1994 | Beltz .................. | A61M 1/3472 |
| | | | 604/4.01 |
| 8,951,484 B2 | 2/2015 | Bersano-Begey et al. | |
| 9,090,865 B2 | 7/2015 | Di Carlo et al. | |
| 9,250,242 B2 | 2/2016 | Martin et al. | |
| 9,494,500 B2 | 11/2016 | Chang et al. | |
| 2003/0134416 A1 | 7/2003 | Yamanishi et al. | |
| 2005/0095155 A1* | 5/2005 | Blight ................. | A61M 3/0201 |
| | | | 417/477.13 |
| 2005/0284815 A1 | 12/2005 | Sparks et al. | |
| 2010/0326916 A1 | 12/2010 | Wrazel et al. | |
| 2011/0244443 A1 | 10/2011 | van Rijn et al. | |
| 2011/0294187 A1 | 12/2011 | Toner | |
| 2012/0063971 A1 | 3/2012 | Carlo et al. | |
| 2013/0255361 A1 | 10/2013 | Juncker et al. | |
| 2014/0113324 A1 | 4/2014 | Di Carlo et al. | |
| 2014/0224710 A1 | 8/2014 | Di Carlo et al. | |
| 2015/0285808 A1 | 10/2015 | Nagrath et al. | |
| 2016/0077097 A1 | 3/2016 | Rao et al. | |

FOREIGN PATENT DOCUMENTS

| | | | | |
|---|---|---|---|---|
| WO | WO-2012172341 A2 * | 12/2012 | .......... | A61M 1/3679 |
| WO | WO-2015128475 A1 * | 9/2015 | ............... | A61L 2/00 |

OTHER PUBLICATIONS

Smyth et al., Modeling, identification, and flow control for a microfluidic device uisng a peristaltic pump, IEEE, (Jul. 2020).
Klespitz et al., Peristaltic pumps—a review on working and control possibilities, IEEE, 191-194, (Jan. 2015).
Kim, et al.; "A temporary indwelling intravascular aphaeretic system for in vivo enrichment of circulating tumor cells;" Nature Communications https://doi.org/10.1038/s41467-019-9439-9 (2019).
Kim, et al.; "A temporary indwelling intravascular aphaeretic system for in vivo enrichment of circulating tumor cells;" Nature Communications https://doi.org/10.1038/s41467-019-9439-9 (2019). Supplementary Information.
Stott, Isolation of Circulating Tumor Cells Using a Microvortex-Generating Herringbone-Chip, Proceedings of the National Academy of Sciences, vol. 107, No. 43, pp. 18392-18397 (Oct. 26, 2010) (http://www.pnas.org/content/107/43/18392.full <https://protect-us. mimecast.com/s/qO6JBKTo7YluK>).
Klarhoefer et al., High-resolution blood flow velocity measurements in the human finger, Man. Reson. Med., 45(4): 716-719, (Apr. 2001).
Stott, et al., Isolation of circulating tumor cells using a microvortex-generating herringbone-chip, Proc. Natl. Acad. Sci., 107(43): 18392-18397, (2010).

* cited by examiner

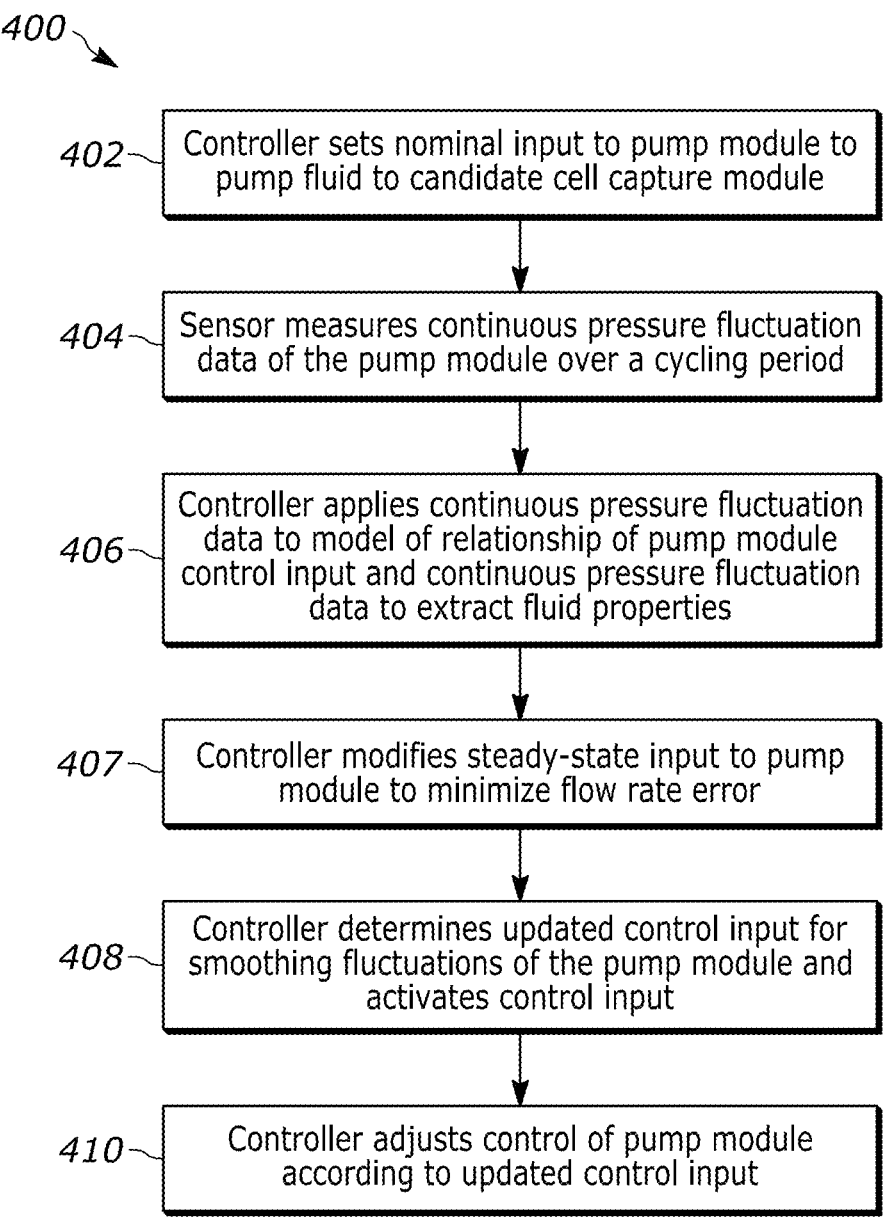

400

402 — Controller sets nominal input to pump module to pump fluid to candidate cell capture module 404 — Sensor measures continuous pressure fluctuation data of the pump module over a cycling period 406 — Controller applies continuous pressure fluctuation data to model of relationship of pump module control input and continuous pressure fluctuation data to extract fluid properties 407 — Controller modifies steady-state input to pump module to minimize flow rate error 408 — Controller determines updated control input for smoothing fluctuations of the pump module and activates control input 410 — Controller adjusts control of pump module according to updated control input

FIG. 7

MICROFLUIDIC FLOW CONTROL USING DIRECT-CURRENT PERISTALTIC PUMP

FIELD OF THE DISCLOSURE

The present disclosure relates to cancer cell related monitors and, more particularly, to a device for capturing circulating tumor cells.

BACKGROUND

The background description provided herein is for the purpose of generally presenting the context of the disclosure. Work of the presently named inventor, to the extent it is described in this background section, as well as aspects of the description that may not otherwise qualify as prior art at the time of filing, are neither expressly nor impliedly admitted as prior art against the present disclosure.

Cancer metastases arise from circulating tumor cells (CTCs) that are shed from the primary tumor and circulate through lymphatic channels and blood. Although identified more than 150 years ago, until recently, CTCs were difficult to detect, enumerate, and characterize. Using modern technologies, several studies have now demonstrated that elevated levels of CTC isolated from a single blood draw may be biomarkers for patients with various carcinomas and are prognostic in patients with metastatic breast, colorectal, prostate, and lung cancers, as well as early stage breast and prostate cancers. Furthermore, CTC analysis holds promise for predicting benefit from targeted therapies, pharmacodynamic monitoring during treatment, and insight into the biology of metastases. Indeed, CTC evaluation might be used for early detection of malignancy, if an assay with sufficient sensitivity and specificity could be developed.

CTCs are extremely rare events. For example, in a single 7.5 mL tube of whole blood drawn from an average patient with metastatic breast cancer, it is unusual to identify more than 10 CTCs within the context of billions of erythrocytes and millions of leukocytes normally present. More than a hundred ex vivo CTC capture devices have been developed to enrich and isolate CTC from whole blood. However, CTC isolation using these technologies is limited to small blood volumes (usually 1-50 mL) due to patient safety concerns, and therefore the absolute number of CTC is small. Moreover, a single blood draw interrogates only those CTC present at the time of venipuncture, and does not take into account temporal differences in CTC release into the circulation. Current methods for interrogating CTCs result in statistical variability and inaccurate reflection of tumor cell heterogeneity. Generally speaking, there is a need for an ability to interrogate larger blood volumes over extended periods to enhance the number of CTCs available for enumeration, and thereby increase statistical confidence of sampling for comparison of serial levels. Doing so could also provide more CTCs for molecular phenotyping, genotyping, and further biological characterization.

Microfluidic devices allow for miniaturization of complex fluid manipulation and, as a result, have been proposed for CTC capture. Microfluidic devices can offer a lower cost and smaller size alternative to more common laboratory analytical capture equipment. Nonetheless, despite advances in microfluidic device capabilities, implementation of control systems for fluid flow through these microfluidic devices is lacking, in particular when trying to capture CTCs.

Commonly, microfluidic systems use syringe pumps to regulate pressure and flow rate through the system. However, syringe pumps are large and do not provide dynamic control of the fluid flowing through them, a problem that escalates over long periods of time. While comprehensive flow control instruments targeting microfluidic applications have begun to appear commercially, these systems are likewise large and expensive relative to the rapid, low-cost fabrication featured by many microfluidic chips.

There is a need for fluid flow management and control systems that may be used with microfluidic devices to provide more effective indwelling solutions for capturing CTCs.

SUMMARY

In accordance with an example, a device for capturing circulating candidate cells from blood, the device including: a housing having a fluid inlet channel to receive the blood from the vasculature of a subject and a fluid outlet channel to return the blood to the vasculature; a peristaltic pump module encapsulated within the housing and fluidly coupled to the inlet channel to receive the blood at a first flow rate and to convert to a second flow rate and output the blood from a pump outlet channel at the second flow rate; a candidate cell capture module within the housing and having a microfluidic capture stage to capture the circulating candidate cells with the blood from the vasculature before providing the return of the blood to the vasculature; and a control system to control operating characteristics of the peristaltic pump module, the control system having a pressure sensor to measure continuous pressure fluctuations of the peristaltic pump module and a feedback control configuration to adjust the operating characteristics of the peristaltic pump module in response to the measured continuous pressure fluctuations.

In an example, the pressure sensor is positioned to measure the continuous pressure fluctuations at an output end of the peristaltic pump module.

In an example, the pressure sensor is positioned to measure the continuous pressure fluctuations at an interim position of the peristaltic pump module proximal to an output end of the peristaltic pump module.

In an example, the control system is configured to compare the continuous pressure fluctuations from the pressure sensor to a reference pressure corresponding to an input end of the peristaltic pump module and from the comparison determine a change in the operating characteristics of the peristaltic pump module.

In an example, the control system is configured to determine the change in the operating characteristics by applying the comparison of the continuous pressure fluctuations to the reference pressure to a predicted flow rate versus pressure model of the control system.

In an example, the continuous pressure fluctuations comprise pressure frequency, pressure amplitude, and/or pressure waveform fluctuation.

In an example, the pressure sensor is to measure the pressure frequency, pressure amplitude, and/or pressure waveform fluctuation after fluid has passed through a fluidic resistor at an output end of the peristaltic pump module.

In an example, the control system is configured as a proportional-integral-derivative (PID) control system.

In an example, the feedback control configuration is to adjust the operating characteristics of the peristaltic pump module in response to the measured continuous pressure fluctuations by adjusting a periodic voltage signal to the peristaltic pump module to reduce subsequent measured continuous pressure fluctuations.

In an example, the feedback control configuration is to adjust the operating characteristics of the peristaltic pump module in response to the measured continuous pressure fluctuations by adjusting a periodic voltage signal to the peristaltic pump module to reduce fluctuations in pressure frequency, pressure amplitude, and/or pressure waveform.

BRIEF DESCRIPTION OF THE DRAWINGS

FIG. 7 illustrates an example process for capturing circulating candidate cells as may be implemented by the system of FIG. 1 and/or the architecture of FIG. 2, in accordance with an example.

Figure 1B:
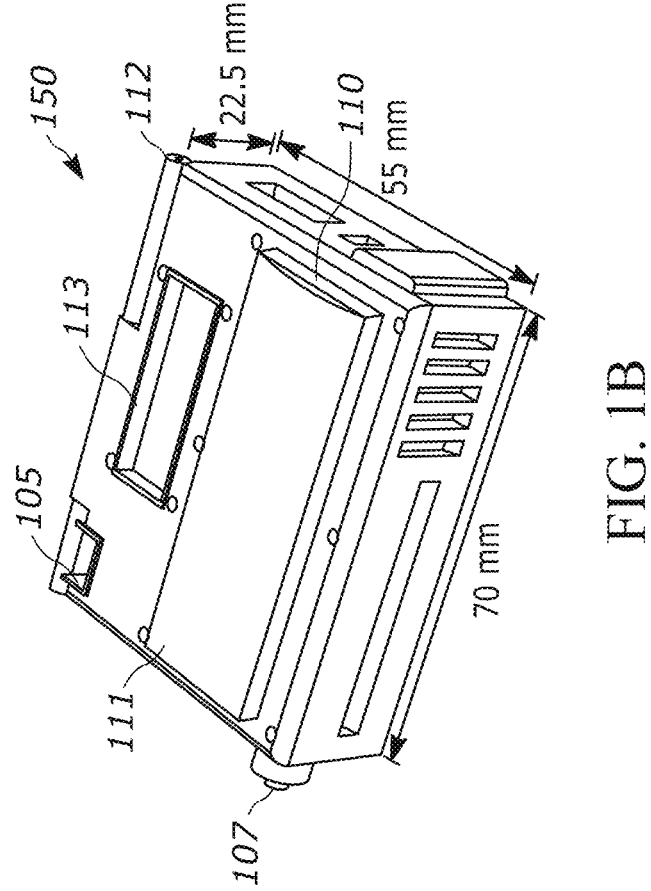
FIG. 1B is an illustration of a compact 3D printed structure for housing components of the system of FIG. 1A, in accordance with an example.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

The apparatus and method components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

DESCRIPTION

The present techniques describe flow control systems using peristaltic pumps, pressures sensors, and configured microcontrollers. The flow control systems described, for example, may be implemented in high throughput microfluidic devices to regulate blood flow through the device. In some examples, these techniques are implemented in microfluidic device that use inertial focusing to isolate circulating tumor cells (CTCs). To obtain optimal focusing of CTCs, for example, flow control systems herein may control the flow rate of blood through the device based on fluid properties that change dynamically. For example, flow control in a CTC capture device may depend on viscosity of the blood, yet blood viscosity may vary among individuals or over time by a factor of approximately 5 to 10, as a function of hematocrit. With the present techniques fluid control systems using dynamic sensing of fluid properties and adjustment in response thereto are able to adjust for such changes in viscosity.

In various examples, flow control systems implement a model for a peristaltic pump driving a microfluidic load, with determination of viscosity via transient dynamics, and identification of nonlinear behaviors in fluid properties that are used in a pressure-based feedback control. For example, by analyzing the transient behavior of pressure within the system, a relative viscosity of a fluid flowing through the microfluidic device can be determined through comparison to a control liquid with a known viscosity. In addition, in some examples, the extended Bernoulli equation, Navier-Stokes equation, and motor dynamics may be used to augment steady-state peristaltic pump models to describe observed nonlinear behaviors in dynamic and quasi-steady-state operation.

In further examples, to control the pressure at the inlet of a microfluidic device, the present techniques may be implemented using a proportional-integral-derivative (PID) control system. In some examples, the parameters of the PID controller may be altered to maintain desirable pressure profiles for driving the microfluidic flow, in response to measurements of the density and viscosity of the liquid flowing through the microfluidic device.

The present techniques may be implemented in temporary indwelling, intravascular aphaeretic candidate cell isolation systems, also termed microfluidic devices herein. These systems may be worn by a patient for several hours to several days, in some examples. The systems are able to interrogate relatively large volumes of carrier fluid, such as blood, for capture candidate cells continuously within that carrier fluid. These systems may operate at normal patient blood flow rates allowing the system to collect blood from the patient and return blood to the patient, at normal blood flow rates, thereby creating an indwelling structure that may be worn by the patient over time. The systems described allow for interrogation of larger blood volumes than classic phlebotomy specimens over a prolonged period of time. The devices herein may be implemented ex vivo or in vivo to capture CTCs or other candidate cells and particles.

Figure 1A:
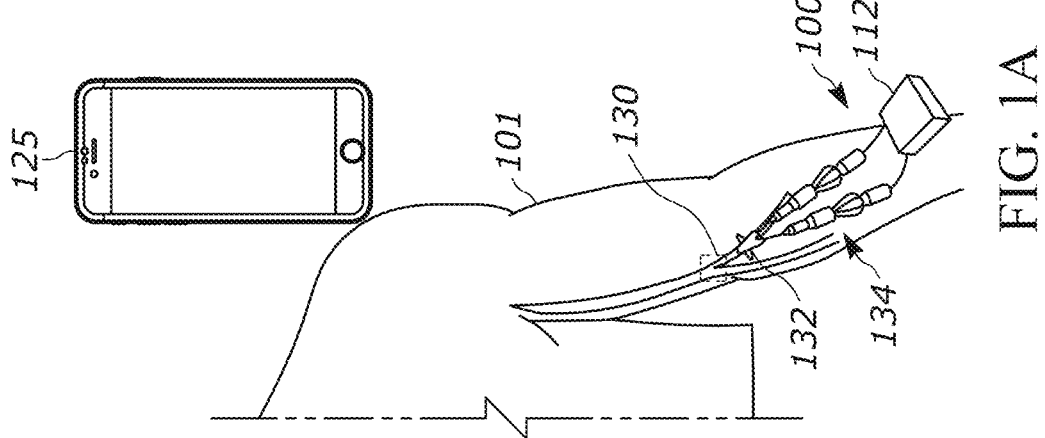
FIG. 1A is an illustration of an example system for performing in vivo detection of circulating tumor cells (CTCs), in accordance with an example.
Figure 1C:
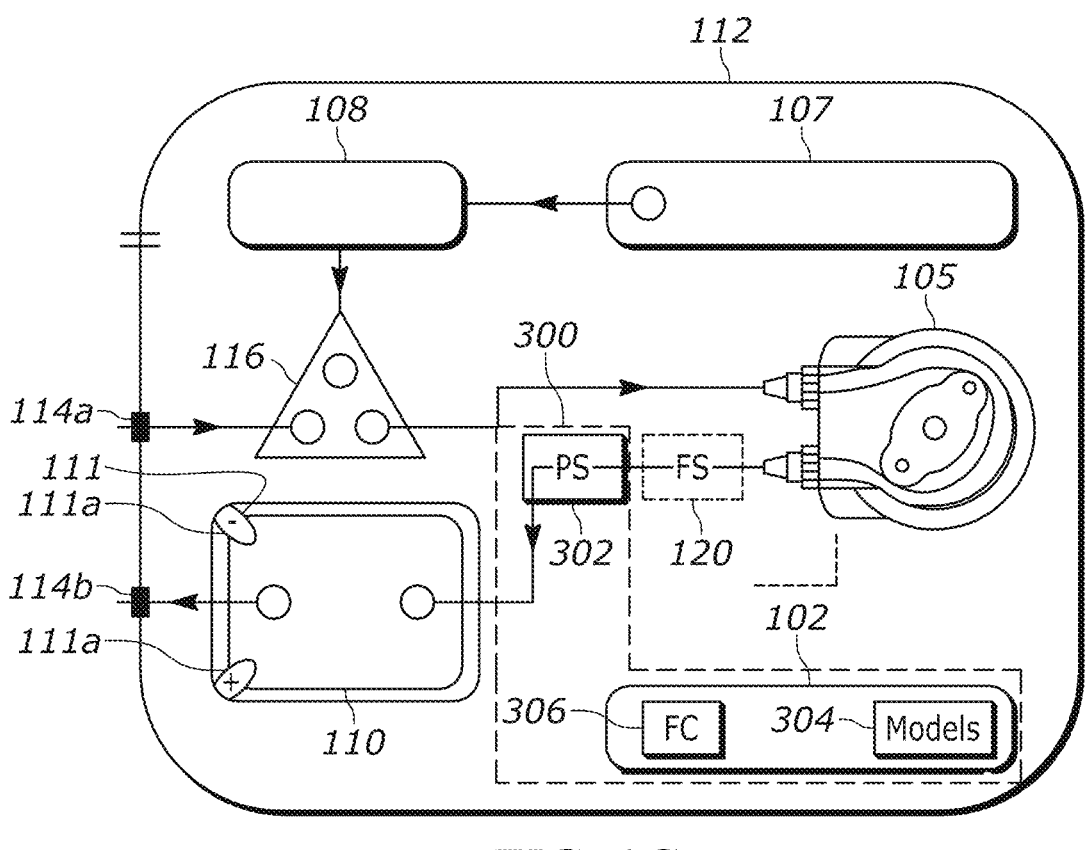
FIG. 1C is a schematic diagram of the system of FIG. 1A for performing in vivo detection of CTCs, in accordance with an example.

An overall design of an example system 100 of the techniques herein is illustrated in FIG. 1A. In the example system 100 of FIG. 1A, each functional component is integrated into a compact structure 150 (e.g., a 3D printed structure), illustrated in example detail in FIGS. 1B and 1C. FIG. 1C is a schematic diagram of the system 100. The structure 150 allows the system 100 to be portable enabling long term use of the system 100 by a subject 101 to interrogate larger volumes of carrier fluid of the subject 101.

The system 100 may be controlled through a custom built mobile application via wireless communication with a control device 125. The control device 125 may be a cellular device, a tablet, a computer, a network, or another device in communication with the system 100 and capable of controlling the functionality of the system 100. In the illustrated example, the system 100 includes four main parts: a microcontroller 102, peristaltic pump 105, heparin injector 107, and a candidate cell capture module 110 (e.g., a CTC capture module). The peristaltic pump 105 may be a self-contained pump module, e.g., that can be inserted into and removed from the housing 112. In other examples, the pump 105 is implemented as a pump module integrated into the housing 112. The capture module 110 contains a microfluidic capture stage in the form of a microfluidic capture chip, encapsulated fully or partially within the housing 112. The system 100 is designed to accommodate any type of CTC isolation device, as long as it is configured to fit into the housing 112 or form part of the housing 112. The housing 112 may have a fluid inlet channel 114a and a fluid outlet channel 114b. Additionally, the housing 112 may be attachable to a wearable mount (e.g., a mount on a belt, wearable strap, article of clothing, glove, etc.) for releasable attaching of the housing 112 to an exterior of a patient. As such, a user of the system 100 may be mobile during operation of the system 100.

In embodiments, the housing 112 includes a receptacle engagement 111. The receptacle engagement 111 configured to physically couple to the candidate cell capture module 110 to hold the candidate cell capture module 110 in place. The receptacle engagement 111 may be configured to form a fluidly sealed engagement between the candidate cell capture module 110 and the housing 112. The candidate cell capture module 110 may couple to the receptacle engagement 111 in a manner that allows for removal of the candidate cell capture module 110 allowing for the replacement of one candidate cell capture module with a different candidate cell capture module. Therefore, the receptacle engagement 111 enables modular functionality of the candidate cell capture module 110 which may be desired to replace a defecting capture module, replace a saturated capture module, replace a capture module with a module having a different antibody or for detecting a different candidate, or for another reason for replacing one capture module with another capture module.

In embodiments, the receptacle engagement 111 may include a backplane or pocket on the housing 112 as illustrated in FIG. 1B. The candidate cell capture module 110 may be placed in a region supported by the backplane of the receptacle engagement 111 to position the candidate cell capture module 110 for operation of the system 100. FIG. 1C illustrates an example of a receptacle engagement 111 having clips 111a that clip onto the candidate cell capture module 110 to hold the candidate cell capture module 110 in place during operation of the system. In embodiments, the receptacle engagement 111 may include fasteners, clips, fastener bands (e.g., rub bands, elastic bands, etc.), a latch, a screw, a spring clamp, a vice, an adhesive, or another physical and/or mechanical structure to physically affix the candidate cell capture module 110 to the housing 112. Further, the receptacle engagement may include an O-ring, a fluid seal, a suction cup, a gasket, a labyrinth seal, an adhesive, a sealant, a plug, or another seal for forming a fluidly sealed engagement between the candidate cell capture module 110 and the housing 112. In any embodiment, the receptacle engagement 111 may provide a means for physically coupling the candidate cell capture module 110 to the housing 112.

In embodiments, the 3D printed structure 150 may include a region for a display 113. The display 113 may display information pertaining to a current operational status or current measurement of the system 100 (e.g., on, off, an error has occurred, a measurement of CTCs, a blood flow through the system 100, low battery, etc.). In embodiments, the display may include a light emitting diode display, a liquid crystal display, a touch screen, or another display capable of displaying alphanumerics or indicia indicative of a current status or measurement performed by the system 100. In embodiments, the controller 125 may control the display 113 to cause the display 113 to display information.

During example operation, whole blood is routed into the system 100 from a subject's peripheral vein 130 with a single cannulation 132 using a dual-lumen catheter 134 via the efflux lumen illustrated as the fluid inlet channel 114a. The fluid passes through a connector 116, the peristaltic pump 105, one or more sensors, and the CTC capture module 110. The fluid then exits the system 100 and flows back into the subject's circulatory system through the subject's vein 130 via the influx lumen of the catheter 134 labeled as the fluid outlet channel 114b. Each end of the catheter 134 is connected to a silicone tube, treated with anticoagulation reagents, with luer lock adaptors that thread into the peristaltic pump 105 and the CTC capture module 110 forming a closed loop structure. In operation, the blood flow may be driven by the peristaltic pump 105 with a preprogrammed flow rate and total processing volume. In embodiments the pump 105 may be a gear pump, diaphragm pump, a plunger pump, piston pump, bellows pump, lobed pump, flexible-vane pump, nutating pump, peristaltic pump, a centrifugal pump, a diffuser pump, a volute pump, a propeller, a mixed-flow pump, a peripheral pump, or another pump capable of pumping fluid.

In various embodiments, the one or more sensors may be a pressure sensor 302 alone, a flow rate sensor 120 alone, or a both sensors. In an examples having the optional flow rate sensor 120 (shown in dashed lines in FIG. 1C), the sensor 120 monitors the blood flow from the peristaltic pump 105 and maintains a constant flow through by providing feedback flow rate data on the monitored blood flow to the controller 102 and/or to the controller 125. In response, the controller 102 and/or controller 125 sends instructions to the pump 105 to increase or decrease the rate of flow of the blood. In some embodiments, the flow rate sensor 120 is configured to measure only the second flow rate, i.e., of the fluid exiting the pump 105. In some examples, the flow rate sensor 120 is configured to measure the first flow rate, i.e., of the fluid (which may optionally include heparin) entering the pump 105. In some embodiments, the flow rate sensor 120 is configured to measure both the first and second flow rates.

By virtue of these different configurations, the controller 102 and/or the controller 125 may control the operating parameters (and thus operation) of the heparin injector 107 to provide heparin to blood or another fluid according to the monitored measured flow rate(s). The controller 102 and/or the controller 125 may control of the pump 105 by adjusting operating parameters of the pump 105. A single flow rate sensor module may be implemented to measure both the first flow rate and second flow rate. While illustrated as being a single flow rate sensors, multiple flow rate sensors may also be configured to measure the first flow rate and/or second flow rate. In embodiments, the first and/or second flow rates may independently be between and including 1 and 50 μL/min, 20 and 100 μL/min, 100 and 200 μL/min, or greater than 200 μL/min. In embodiments, the first flow rate may be below a normal blood rate for a patient, which may be patient dependent based on an average blood flow rate of the patient.

In the illustrated example, the system 100 includes a control system 300 that includes the controller 102 and the pressure sensor 302 that measures continuous pressure fluctuations in fluid and provides that data to the controller 102. The pressure sensor 302 is illustrated as positioned to measure pressure fluctuations of a fluid exiting the pump 105, and in particular, fluid measured after passing through the flow rate sensor 120. In other embodiments, the pressure sensor 302 may be upstream of the flow rate sensor 120 measuring continuous pressure fluctuations of the fluid from the pump 105 before that fluid is passed to the flow rate sensor 120. In yet other embodiments, the pressure sensor 302 may be placed to measure pressure at an interim location within the pump 105. In some examples, the continuous pressure fluctuation data measured by the sensor 302 is pressure frequency data, pressure amplitude data, and/or pressure waveform fluctuation data.

In some embodiments, the controller 102 includes one or more models 304, e.g., peristaltic pump operation models and predicted flow rate versus pressure models. The controller 102 provides received continuous pressure fluctuations to the one or more models 304 that generate data provided to a feedback controller 306 that controls operation of the peristaltic pump 105 control in accordance with one or more techniques and methods described herein. The feedback controller 306 may be implemented in different configurations, e.g., a repetitive feedback control, an internal model feedback control, or a periodic feedback control. The feedback controller 306 may be configured to continuously or periodically poll sensor 302 (and/or optional sensor 120) to capture continuous pressure fluctuation data for a cycling period of the peristaltic pump 105.

Figure 2:
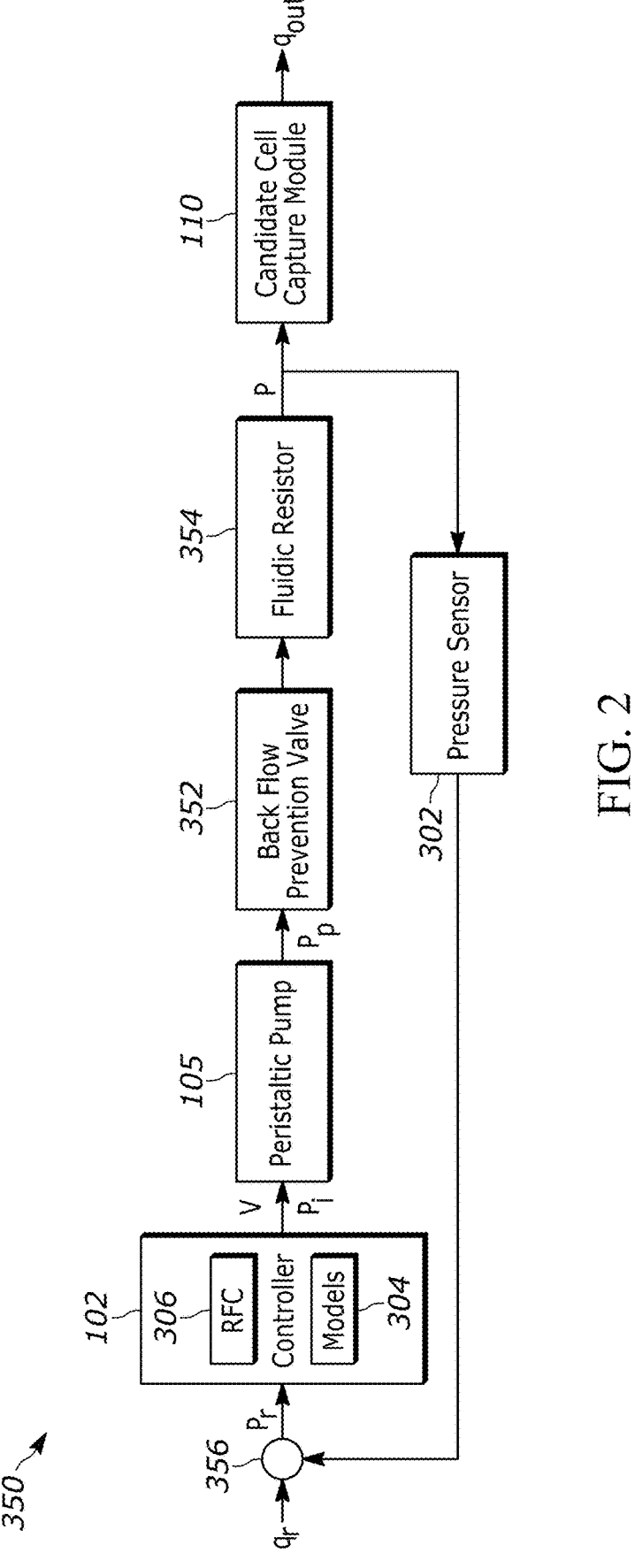
FIG. 2 is a diagram of an example architecture for microfluidic flow control using a peristaltic pump and a continuous pressure fluctuation measurements using pressure versus flow rate system models, in accordance with an example.

FIG. 2 illustrates an architecture 350 of a controller operation of a microfluidic device in an embodiment. Given a target flow rate, $q_r$, given an identified fluid viscosity, a reference pressure, $P_r$, is specified for closed loop control of the peristaltic pump 105 (via an input voltage, V) by the controller 102 to ensure an output flow rate, $q_{out}$, tracks the target flow rate is dependent a measurement of continuous pressure fluctuations and viscosity in the microfluidic device.

In the illustrated embodiment, the architecture 350 includes the peristaltic pump 105, a backflow prevention valve 352, a fluidic resistor 354, the pressure sensor 302, and the microfluidic device (e.g., candidate cell capture module) shown schematically in FIGS. 1A-1C. In some examples, the fluid originates in a reservoir at atmospheric pressure. For indwelling systems, the fluid originates in the reservoir at vein pressure which is about 7-14 mmHg in normal patients. The fluid then passes through the peristaltic pump 105, which adds energy to the fluid increasing the pressure within the fluidic system. The fluid then passes through the backflow prevention valve 352, which increases the efficiency of the peristaltic pump 105 by preventing the fluid from flowing back out of the input of the peristaltic pump 105. The fluid next passes through the fluidic resistor 354 to decrease the sensitivity of the pressure measured within the fluidic system as it relates to the change in power provided to the peristaltic pump 105. The fluid then flows over the pressure sensor 302 connected to the main line by a T-connector. After passing the pressure sensor 302, the fluid flows into the candidate cell capture module 110 through one inlet and out of the capture module 110 from four outlets to atmospheric conditions. In closed loop operation, at the controller 102, the sensor pressure, P, is compared to a reference pressure, $P_r$, through data combiner 356 or other closed loop element. That reference pressure may be stored within the controller 102. In some examples that reference pressure is selected by a reference generator given a desired flow rate, $q_r$, and fluid property information. Note this configuration is such that the outlet flow rate, $q_{out}$, need not be available for direct measurement to nonetheless provide feedback control of the peristaltic pump 105. The controller therefore compares the continuous pressure fluctuations from the pressure sensor to a reference pressure corresponding to an input end of the peristaltic pump, and from the comparison can determine a change in the operating characteristics of the peristaltic pump, for example, by supplying comparison data to a predicted flow rate versus pressure model from which voltage control input for the pump is generated.

In an embodiment, 12 Volt peristaltic pump (available from Adafruit Industries of New York) was used to generate flow through the candidate cell capture module. Pump peristalsis was based on compressing and relaxing segments of a compressible tube, with the compression drawing the fluid in and the relaxation moving the fluid away from the pump. Compression elements were driven circumferentially around the tubing by a DC motor, but due to finite length of the flexible tube, oscillatory behavior was present in the pump flow and pressure output that is generally not present when using a syringe pump.

In an embodiment, the pump 105 was operated in both open- and closed-loop using a Raspberry Pi microcomputer. All programming was done using a Virtual Network Computing (VNC) network connection. Pulse width modulation (PWM) was used to generate analog voltages during control from a fixed voltage source. A L298N motor driver was used to increase the current provided from the Raspberry Pi and accommodate the 12V external voltage required by the peristaltic pump.

Pressure sensing was done using a High-accuracy Silicon Ceramic (HSC) 0-10 bar 3.3V pressure sensor (available from Honeywell). The HSC sensor is a piezoresistive silicon pressure sensor that works by increasing resistance through the circuit as pressure is applied to a piezoresistive element in the sensor. The HSC sensor provides a tight accuracy (+0.25%) which reduced the software needed to correct system inaccuracies.

Figure 3:
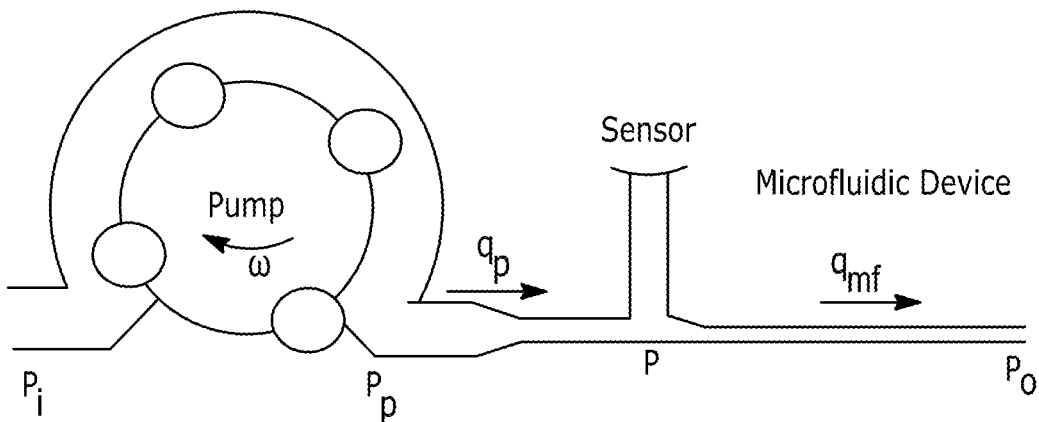
FIG. 3 is a schematic of an example model of pressure versus flow rate that may be used in the architecture of FIG. 2, in accordance with an example.
Figure 4:
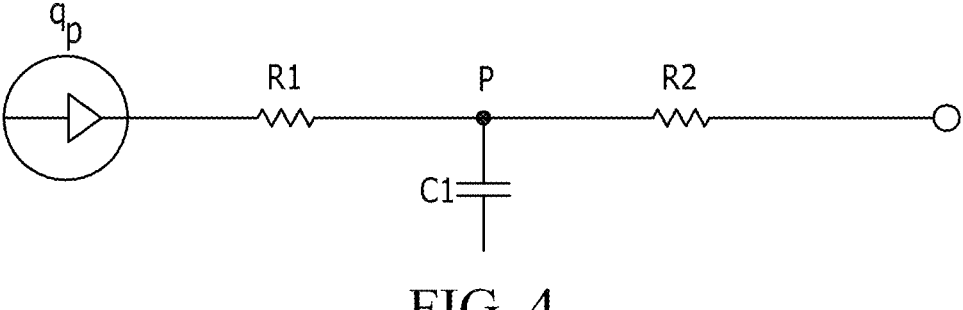
FIG. 4 illustrates a circuit schematic model of a fluid flow from a peristaltic pump that may correspond to the example model of FIG. 3, in accordance with an example.

In various embodiments, the controller 102 includes one or more models 304 of operation of system 100 or system 350. For example, to model the relationship between pump voltage input, measured pressure, and pump and first and second flow rates of the cell capture module, a dynamic model may be constructed by augmenting flow descriptions of peristatic pump operation. FIG. 3 illustrates an example model that may be stored as an interrelated model of variables in the models 304, where Pi is pump input pressure, ω is the peristatic pump's angular velocity, Pp is pressure at the pump output, $q_p$ is the flow rate at the pump output (e.g., entering the first fluidic resistor), P is the measured pressure, qmf=qout is the flow through the microfluidic device (e.g., the candidate cell capture module), and $P_o$ is the outlet pressure. The fluidic elements in the architecture 350 can be described by an equivalent electrical circuit with a current supply, two fluidic resistors, and a capacitor, as shown in FIG. 4. The first fluidic resistor, R1, is the discrete resistor added to partially smooth pressure between the pump and sensor; the fluidic capacitance, C1, occurs due to compliance in tubing of the first resistor and T-connector to the pressure sensor; and the second resistor, R2, is the resistance of the microfluidic chip.

In an embodiment, in one or more the models 304, the Darcy-Weisbach equation for head loss in a laminar flow was used to model the fluidic resistance of the candidate cell capture module. By simplifying the Darcy-Weisbach equation, the pressure loss from the capture module was modeled as $$P_{loss} = K\mu\mu_{avg} \tag{1}$$

where $P_{loss}$ is the pressure drop across the capture model, e.g., the microfluidic chip, (i.e. $P_{loss} = P - P_o$), $\mu$ is the viscosity of the fluid, $\mu_{avg}$ is the mean flow velocity through the microfluidic channels, and K is a constant to be identified. As the microfluidic channels of the capture module may be rigid, mean velocity can be treated as proportional to flow rate, and the capture module can be represented as a viscosity dependent fluidic resistor, $$R_2 = \frac{P - P_o}{q_{mf}} = K'\mu \tag{2}$$

where K' is a constant proportional to K.

Taking atmospheric pressure as the pressure reference and equal to inlet and outlet pressures, the passive fluid dynamics become:

$$C\frac{dp}{dt} = -\frac{P}{K'\mu} + q_p. \tag{3}$$

In the embodiment, electromechanical pump dynamics were represented with a conventional DC motor model, $$V - L\frac{di}{dt} - Ri - K_m\omega = 0 \tag{4}$$

$$J\frac{d\omega}{dt} = K_m i - B\omega - \tau_f \tag{5}$$

where V is input voltage, i is motor current, L is internal inductance, R is internal resistance, and Km is a motor constant, J is the effective pump inertia, B is viscous drag, and vf is resistance torque arising from dry friction and other mechanical resistance between rotating compression elements and their connectors and pump tubing. For simplicity, in an embodiment, the model assumed that all pump operation occurs beyond the startup torque of the pump (i.e., Kmi>vf for operating conditions to be considered).

As stated, in various embodiments, the pressure sensor 302 measures pressure and continuous pressure fluctuation characteristics (e.g., frequency, amplitude, waveform). Fluctuations in the peristaltic pump output may arise due to the continuous compression and relaxation of the pump tubing. For one or more models, an energy analysis based on the extended Bernoulli equation was used to relate the pressure and flow outputs of the pump to behavior downstream at the pressure sensor and the capture module. The change in pressure from pump inlet to pump outlet was modeled as $$P_p - P_o = \frac{\dot{W}_{pump}}{q_p} + \frac{\overline{u}_{x=0}^2 - \overline{u}_{x=\lambda/4}^2}{2}\rho \tag{6}$$

where $\dot{W}_{pump}$ is the power imparted from the pump to the fluid, p is fluid density, and $\overline{u}_{x=0}^2$ and $\overline{u}_{x=\lambda/4}^2$ are the mean squared velocities of flow at the inlet and outlet of the pump A sinusoidal wave, d(x,t), was used to model the alternating relaxation and compression of the tubing created by the peristaltic pump, following prior work by Latham, "Fluid Motions in a Peristaltic Pump," MIT Libraries pp 13-21, July 1966 on modeling flow behavior within peristaltic pumps:

$$d(x, t) = a + b\sin\left(\frac{2\pi}{\lambda}(x + ct)\right) \tag{7}$$

where x is the linear distance along the tube, a is the average thickness of the tube, b is the compression amplitude, A is the length of one oscillation, and c is the resulting wave speed. The relative outlet position x=λ/4 in Eq. (6) was selected based on the geometry of the pump, with the outlet located approximately one quarter wavelength beyond an integer number of compression elements in the pump.

Simplifying the general form of the Naiver-Stokes equation with the conditions of incompressibility and continuity as done by Latham, "Fluid Motions in a Peristaltic Pump," MIT Libraries pp 13-21, July 1966, flow at specific points in the tubing in a peristaltic pump, u(x, y, t), can be shown to take the form:

$$u(x, y, t) = c - \frac{1}{2\mu}\frac{dP}{dx}\left(d(x, t)^2 - y^2\right) \tag{8}$$

where y is the position in the thickness direction of the pump tubing. Integrating over the tube thickness, mean flow at a given point within the pump becomes:

$$\overline{u}(x, t) = c - \frac{1}{3\mu}\frac{dP}{dx}d(x, t)^2 \tag{9}$$

Equations (8) and (9) were generated based on assumptions of steady-state behavior within the pump, and thus neglect dynamic effects that may occur within the fluid inside the pump, but we find the assumed forms effectively capture pump behavior observed experimentally.

Energy transmitted to the fluid inside the pump was modeled as the electrical power to the pump minus any electrical and mechanical losses, $\dot{W}_{loss}$, or $$W_{pump} = iV - \dot{W}_{loss} \tag{10}$$

Various forms could be assumed for $\dot{W}_{loss}$ as a function of viscosity, voltage, or other factors, depending on the model.

Output flow from the pump was assumed to be geometrically related to average speed at the endpoint of peristaltic wave, or $$q_p = w\overline{u}(\lambda/4,t)d(\lambda/4,t) \tag{11}$$

where w represents the effective width of the tube. Modeling the attached fluidic resistor R1 as also being viscosity-dependent (R1=R1'μ), Equations (6), (10), and (11) produce a final nonlinear model for the relationship between pump output flow, input voltage, and measured pressure at the microfluidic device (e.g., candidate cell capture module) inlet, $$q_p\left(P + R_1'\mu q_p + \frac{q_p^2}{d^2}\psi\right) = iV - \dot{W}_{loss} \tag{12}$$

which can be solved by the controller 102, and in particular by the feedback controller 306, in parallel with Equations (3)-(5) to simulate the fluid response, from which operating characteristic of the pump 105 can be adjusted, for example, by adjusting the voltage applied to the pump 105.

The foregoing example model for approximating dynamic behavior of the peristaltic pump attached to the candidate cell capture module should be calibrated to identify various parameters. Certain parameters, such as a, b, and A, are known from pump geometry. Others were identified from observed system behavior. To calibrate and finalize the model, viscosity measurement from transient pressure response was developed and then the pump pressure to flow relationship was reformulated to provide a small set of constants.

Viscosity Identification: The back-flow prevention valve has been neglected in forced response of the system, where unidirectional, non-zero pump motion allows unidirectional flow to be assumed. However, its presence allows for straightforward identification of viscosity relative to a reference fluid. When the pump is shut-off, fluid dynamics from Equation (3) simplify to $$(CK_\mu')dP/dt = P \tag{13}$$

for a simple first-order linear system with time constant proportional to $\mu$. Once a time constant is calibrated for a fluid with known viscosity (i.e. water), relative viscosity for other fluids (i.e. blood) can be directly computed through extraction of the time constant from free exponential decay of pressure from a pressurized initial condition.

Parameter Identification: Once viscosity is known, models can be further configured with parameters describing other dominant nonlinearities arising from the interaction of the peristaltic pump with the remainder of the system can be found through a series of simplifying assumptions. For example, we assume steady-state operation with dynamics from Equations (3)-(5) neglected and thus qp≈qmf, and substitute Equation (2) into Equation (12):

$$q_p\left(K'\mu q_p + R_1'\mu q_p + \frac{q_p^2}{d^2}\psi\right) = iV - \dot{W}_{loss} \tag{13}$$

Equation (13) incorporates quasi-static behavior from the fluidic resistances and steady-state periodic behavior driven by d(A/4,t) in this simplified form.

Combining the viscosity dependent resistances using a new constant, $\alpha$, we have $$\alpha\mu q_p^2 + \frac{q_p^3}{d^2}\psi = iV - \dot{W}_{loss} \tag{14}$$

This relationship is then linearized about a nominal voltage dependent flow rate, $$q_P = K_q C + \delta g_P \tag{15}$$

where Kq is an assumed steady-state gain from voltage to flow rate for a nominal flow, and is the deviation from this nominal flow given perturbations to viscosity or other effects. Substituting Equation (15) into the Taylor expansion of nonlinear terms in Equation (14) and neglecting higher-order terms produces the relationship $$\alpha\mu(K_q V)^2 + 2\alpha\mu(K_q V)\delta q_p + \frac{(K_q V)^3}{d^2}\psi + 3\frac{(K_q V)^2}{d^2}\psi\delta q_p \approx iV - \dot{W}_{loss} \tag{16}$$

or $$\delta q_p \approx \left(\frac{1}{2\alpha\mu(K_q V) + 3\frac{(K_q V)^2}{d^2}\psi}\right)\left(iV - \dot{W}_{loss} - \frac{(K_q V)^3}{d^2}\psi - \alpha\mu(K_q V)^2\right) \tag{17}$$

Finally, assuming that the periodic fluctuations from the d(t) term in the denominator of Equation (17) are small relative to the contributions of $2\alpha\mu(K_q V)$ and writing Equation (2) in terms of Equations (15) and (17), steady-state behavior is approximated as $$P \approx K'\mu\left|K_q V + \left(\frac{1}{2\alpha\mu(K_q V)}\right)\left(iV - \dot{W}_{loss} - \alpha\mu(K_q V)^2 - \frac{(K_q V)^3}{d^2}\psi\right)\right| \tag{18}$$

To simplify parameter identification, we note that in steady-state, current and angular velocity will have constant and linear voltage-dependent terms resulting from Equations (4) and (5). In addition, it was noted earlier that $\dot{W}_{loss}$ originating in Equation (18) might be dependent on factors such as viscosity or angular velocity. However, if these dependences are also approximately linear (i.e., $\dot{W}_{loss} = f(V, \mu, \omega) \approx c_0 + c_1 V + c_2\mu + c_3\omega$) all candidate effects can be combined in Equation (18) to produce four effective constants regarding sensitivity to voltage and viscosity:

$$P \approx k_1\mu V + k_2 V - k_3\frac{\mu}{V} + \frac{k_4}{d^2} \tag{19}$$

To summarize, the key assumptions leading to the model in Equation (19) are: there exists a nominal voltage-dependent flow rate from which actual flow rate will vary modestly with different fluids (i.e., Equation (15)); periodic fluctuations in pump output arising from the peristaltic process are small relative to the mean output flow, allowing the denominator in Equation (17) to be simplified; and if not constant, energy losses in the pump can be approximated as unknown but linearly dependent on input voltage and viscosity. The approximations producing the model in Equation (19) allow system dependence on viscosity and voltage to be effectively captured using a calibration of four constants.

In various embodiments, the feedback controller 302 of the controller 102 was implemented as an error tracking proportional-integral-derivative (PID) controller was used to regulate the pressure within the microfluidic system, i.e., $$V = K_d\frac{d}{dt}(P_r - P) + K_P(P_r - P) + K_i\int(P_r - P)dt \tag{20}$$

Control gains $K_p$, Ki, and Kd were tuned manually with water to minimize rise time without inducing overshoot. When using other fluids, the control variables were altered in the PID controller based on the inferred viscosity of fluid to make the dynamics defined by Equations (3), (19), and (20) as close as possible to equivalent given the controller form. This primarily affected the value of Kd for the range of fluids tested (water, isopropanol, whole milk, and blood). Finally, to avoid integrator windup, in implementation the integral term was included only after the measured pressure was within 10% of the reference.

In some embodiments, the model 304 and feedback controller 306 may be developed from experimental data. For example, as discussed above, viscosity of fluid in the microfluidic system may be determined by analyzing the transient behavior of the pressure within the microfluidic system after the peristaltic pump is shut down. For example, to set up models and controller operation, a setup process may be performed by running the peristaltic pump at a constant voltage, then shutting the peristaltic pump down until the pressure in the microfluidic system dropped to a predetermined value, e.g., 0.03 bar (gauge). Continue pressure fluctuation data may be collected from the pressure sensor in a sample data set. The transient data may then be analyzed by fitting an exponential function to the data. By comparing the exponent values of different liquids, the relative viscosity of the liquids can be determined, for example in comparing water to whole blood, with both fluids having clean exponential decay but substantially different time constant.

To identify parameters in a simplified nonlinear system model, a step function voltage input can be provided to the microfluidic system starting at 3 Volts and increasing every ten seconds by 1.5 Volts. Two fluids may be used to calibrate viscosity effects, e.g., water and isoproponol. By providing multiple step inputs, constants k1, k2, and k3 determining proportionality to V, µV, and µ/V as dominant features in system behavior, can thus be identified. Meanwhile, constant k4 can be identified from the amplitude of periodic oscillations remaining once the output pressure reaches its mean value at each voltage step. In addition, peristaltic wave velocity, c, while directly dependent pump angular velocity and radius, was not precisely known from pump specifications and was inferred from observed motion.

The resulting simulated versus modeled pressure trajectories during the sequential step inputs can be stored. The effects of nonlinear voltage and viscosity interaction is identifiable in the non-uniform increase in output pressure for each voltage input, as well as the differences in total pressure for the two different liquids. Characteristic periodic oscillations arising from the peristaltic process would likewise be identifiable with similar behavior in both experimental and simulated outputs.

Figures 5, 6:
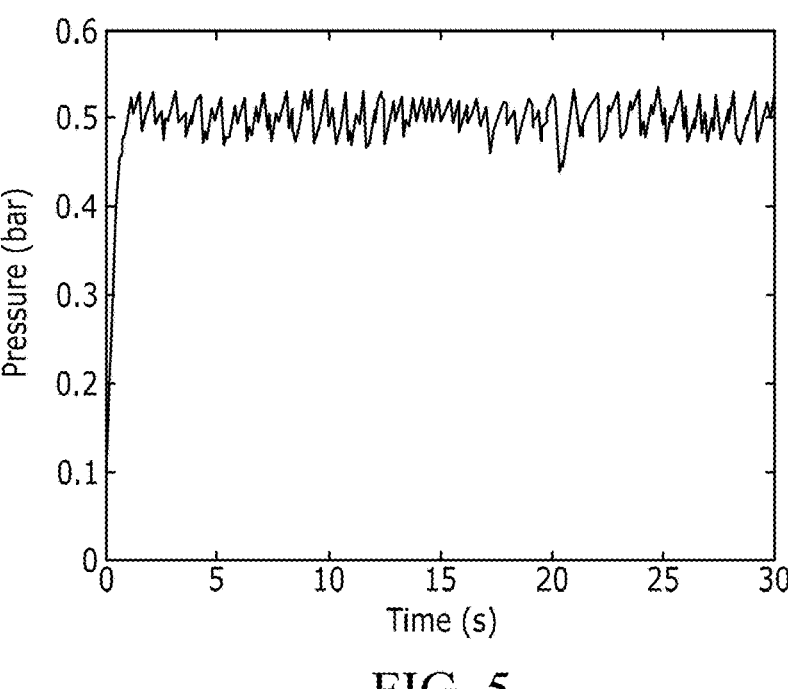
FIG. 5 illustrates a plot of pressure versus time presenting representative pressure profiles for viscosity identification in a model for an example fluid, in accordance with an example.
FIG. 6 illustrates a plot of pressure versus time after peristaltic pump shut down presenting transient decay identification in a model for an example fluid, in accordance with an example.

In application to blood flow control, a target flow rate and associated reference pressure could be specified based on inferred blood viscosity. In an example, for the purposes of controller demonstration, an arbitrary reference pressure of 0.5 bar was used. FIG. 5 shows a sample closed-loop response to isopropanol as the liquid to 0.5 bar reference pressuring using viscosity adjusted PID gains. FIG. 6 illustrates a plot of pressure versus time after peristaltic pump shut down presenting transient decay identification in a model for an example fluid.

Thus as shown, in some embodiments, the present techniques provide a model, system identification procedures, and a controller for a microfluidic system using a peristaltic pump that accommodate a wide range of possible fluid viscosities. Viscosity may be identified from transient open-loop response in comparison to water, and parameters describing nonlinear relationships of the system are identified using sequential step-response data.

FIG. 7 illustrates an example cell capture process 400 that may be implemented by the system 100, for example, using the architecture 200 of FIG. 2. Initially, at a process 402, the controller 102 sets an initial control input signal (e.g., a nominal input) for the peristaltic pump 105 to pump a sample fluid to the candidate cell capture module 110. For example, the pump 105 is to receives a sample fluid, such as blood captured through an indwelling implementation of the system 100, and reduces the flow rate and outputs the sample fluid to the candidate cell capture module 110. At a process 404, the sensor 302 measures continuous pressure fluctuations of the pump 105 over a cycling period. The particular values measured by the sensor 302 may depend on the variables in the stored model 304. In some examples, at the process 404 pressure frequency, pressure amplitude, and/or pressure waveform fluctuation are measured as the continuous pressure fluctuation data. By measurement, it will be understood that in some examples, the sensor 302 measures values from which one or more continuous pressure fluctuation data may be determined at the sensor 302. The process 404 generates the continuous pressure fluctuation over a full pumping cycle of the peristaltic pump, over multipole pumping cycles, or over a fraction of a pumping cycle, so long as the amount of data is sufficient to measure internal fluctuations in pressure experienced within the pump 105. The data from process 404 is provided to the controller in a feedback configuration. The process 404 may continuously measure data, to capture fluctuation data through each cycle and from cycle to cycle. In other examples, the process 404 may periodically measure such data, for example, at the same point in time for each cycle or after multiple cycles.

The fluctuation data from process 404 is provided to process 406, where the controller 102 provides the data to a model (stored as model(s) 304) of the relationship of control input for the pump (such as drive voltage supplied to the pump) and the measured continuous pressure fluctuation data. In some examples, with the model, the controller 102 is able to extract fluid properties. In an example, the model(s) 304 may contain Equation (20), as a model between measured pressure amplitude (P) at an exit of the pump 105, a reference pressure amplitude (Pr) at an inlet position before the pump 105, constants specified for different fluids and viscosities, and the drive voltage for the pump, which is an example control input. In some examples, the models 304 may further include any number of other expressions. For example, the model 304 may include other of the equations (1)-(20) that are to be solved by the controller 102 in determining a control input for the pump, e.g., altering control variables based on the inferred viscosity of sample fluid to make the dynamics defined by Equations (3), (19), and (20) as close as possible to equivalent given.

From the process 406, the controller 102, at process 407, modifies the steady-state control input to the pump module 105 based on the model at process 406 to minimize flow rate error. From the process 407, the controller 102, at process 408, determines any updates to the control input, e.g., changes to the drive voltage (such as any one or more of changes to amplitude, duty cycle, waveform, ramp up time, decay, etc. for the drive voltage. Using the models herein, in some examples, the changes to the control input are intended to smooth out the pressure fluctuations during operation of the pump 105 in subsequent pumping cycles. The updated control input at block 408 may be combined with the adjusted steady-state control input to generate a combined control input signal sent to the pump module 105. This control input may be a periodically updated control input, for example. The controller 102 provides such feedback control of the pump 105 at the process 410.

In this way, the process 400 is a further example of the techniques herein that rely upon models of pump module operation and measure data on internal fluctuations of pressure (such as time varying and position-dependent values) during operation to provide feedback control of the pump for smoothing operation and reducing those fluctuations and thereby improving viscosity consistency of flow rate of the fluid passing to a connect microfluidic capture device. In some embodiments, therefore, the techniques herein are implemented in a repetitive feedback control configuration that relies upon internal models of periodic pump operation. In some embodiments, these models are static. However, in some embodiments, these models are adaptive and thus may be updated in response to measured values from sensors and the feedback configuration. Further, in some examples, the models can provide feedback data in a separate path than already-existing feedback control, to allow for inclusion of the model affects during an already existing feedback control operation. In any of these examples, periodic oscillations or other disturbances that occur during operation can be compensated for resulting in a smoothing of operation of the pump and thus better operation of the connected microfluidic device.

Figure 8:
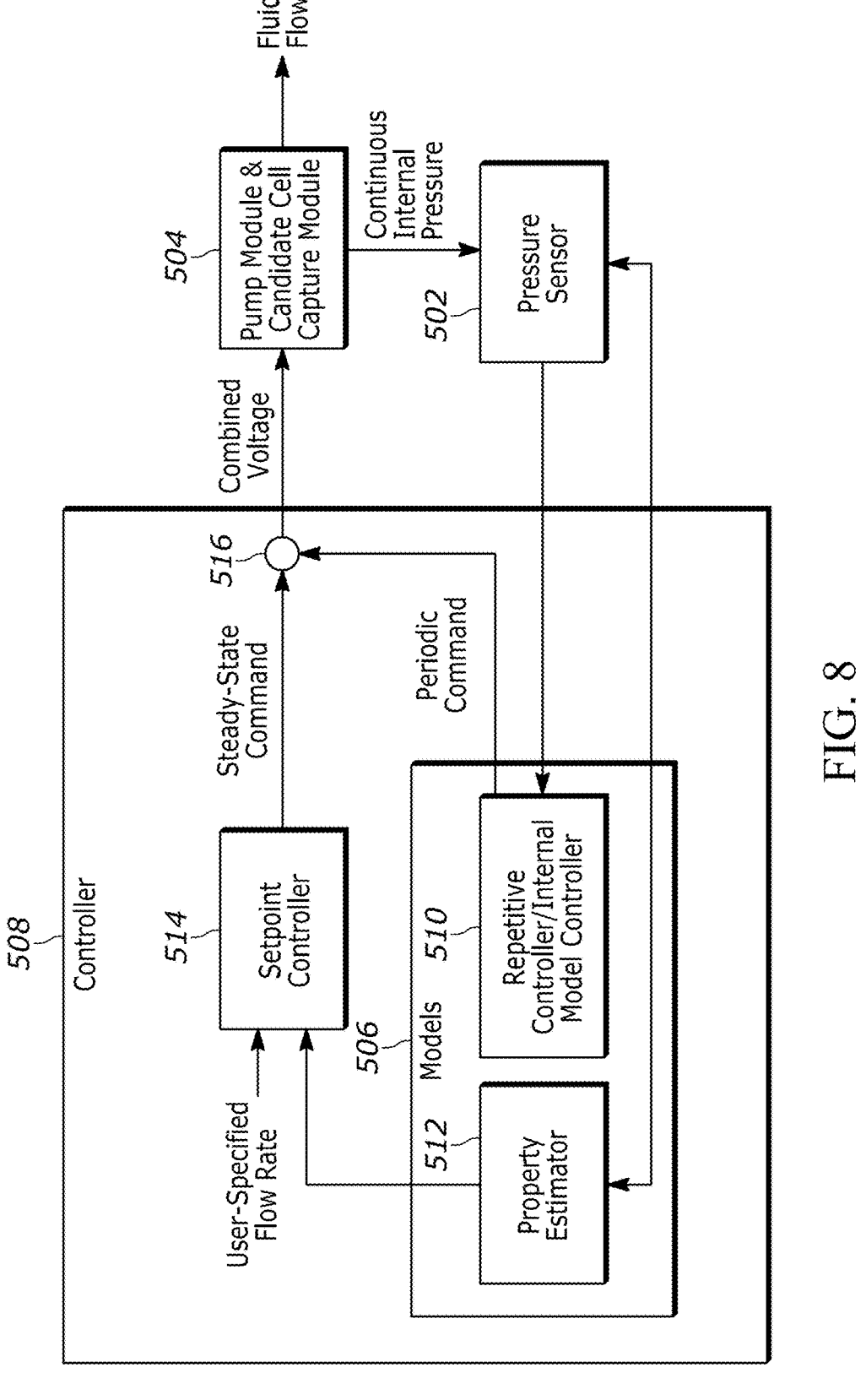
FIG. 8 is a diagram of another example architecture for microfluidic flow control using a peristaltic pump and a continuous pressure fluctuation measurements using pressure versus flow rate system models, in accordance with an example.

FIG. 8 illustrates an architecture 500 of a controller operation of a microfluidic device in another embodiment. A pressure sensor 502 monitors continuous pressure fluctuations in a microfluidic device 504, e.g., having a pump module and candidate cell capture module in accordance with examples herein. As with other examples herein, the continuous pressure data may represent fluctuations into to the rotating pump module. The continuous pressure fluctuations are provided to one or more models 506 stored in controller 508. In the illustrated architecture, the model 506 contains a repetitive controller/internal model controller 510 and a property estimator 512 both receiving pressure data from the sensor 502. In an example, the property estimator 512 is configured to determine a steady-state control input adjustment from the pressure data, e.g., to minimize envelope signal errors such as flow rate errors. The property estimate 512 sends to the steady-state control input adjustment to a setpoint controller 514 for updating a stated-state command input provided by the controller 508. The repetitive controller/internal model controller 510 receives the pressure data from the sensor 502 generates an updated control input (e.g., a period command input) for smoothing fluctuations of the microfluidic device 504 and provides the update to a combiner 516 that combines the signal with the steady-state command input to generate a combined voltage as the control input, which is provided to the microfluidic device 504 to adjust operation and correct fluid properties of the fluid flow output. Thus, as shown, in some examples, the models herein may provide for simultaneous determination of steady-state control input and periodic smooth control input signals both determined in response to internal pressure sensed values.

Figure 9:
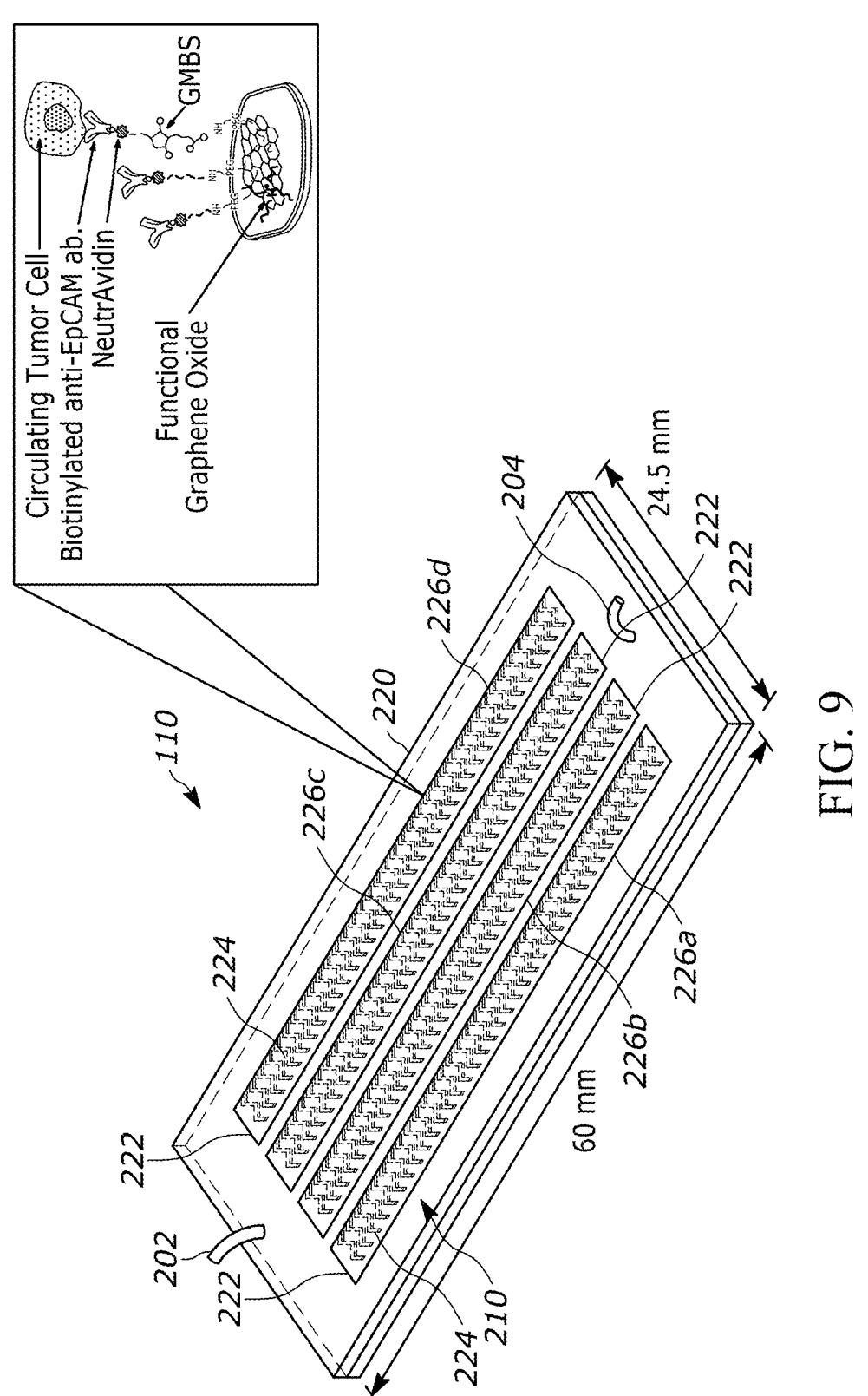
FIG. 9 illustrates of an embodiment of a candidate cell capture module including an inlet, an outlet, and a microfluidic capture stage, in accordance with an example.

FIG. 98 illustrates an embodiment of the candidate cell capture module 110. The CTC capture module 110 of FIG. 9 includes an inlet 202, an outlet 204, and a microfluidic capture stage 210. The capture module 110 may be replaceably mounted inside of the housing 112 and the capture module 110 may form a fluidly sealed engagement with the housing 112. The fluid enters the capture module 110 through the inlet 202, the fluid passes through the microfluidic capture stage 210, and the fluid exits the capture module 110 though the outlet 204. The outlet 204 of the microfluidic capture stage 210 may be in fluid communication with the fluid outlet channel 114*b* of the housing 112 to return the fluid to the vasculature of the patient. The microfluidic capture stage 210 includes a substrate that was exposed to UV, and a polydimethylsiloxane (PDMS) structure that was autoclaved before assembly of the microfluidic capture stage 210. All surface modification steps of the components of the microfluidic capture stage 210 were performed in a sterile, low germ count environment. In examples, the sterility of the devices and channels were measured by determining endotoxin levels using limulus-amebocyet-lysate (LAL) gel clot assay having 0.5 EU/mL sensitivity. The measurements resulted in no positive testing indicating that the endotoxin levels were less than 0.5 EU/ml. The measured endotoxin levels comply with current FDA guidelines of less than 0.5 EUmL for devices that directly or indirectly contact the cardiovascular system.

The PDMS structure and/or the substrate of the microfluidic capture stage 210 may be coated with gold and one or more reagents applied to the resultant gold structures to capture the CTCs. The reagents were sterilized and tested for endotoxin levels using LAL gel clot assay (0.5 EU/mL sensitivity, before the reagent was applied to the surface of the PDMS structure. Before operation of the capture module 110, the microfluidic capture stage 210 was exposed to UV and fluid was exposed to the surface of the microfluidic capture stage 210. The fluid was then sampled, plated on sheep blood agar, and cultured for 2 weeks to detect any bacterial growth. While in an example EpCAM was used as a reagent to capture CTCs, other reagents may be used to capture other candidate cells. For example, CD31 may be used to capture enodethelial cells and miRNA may be captured using other reagents. Therefore, the microfluidic capture stage 210 may be configured to capture any of one or more types of candidate capture cells.

In some embodiments, the microfluidic capture stage 210 is a herringbone graphene oxide CTC chip designed using functional graphene oxide sheets for sensitive capture and chaotic mixing via herringbone structures for enhanced throughput. Example implementations of the herringbone graphene oxide CTC chip are described in U.S. application Ser. No. 17/013,187, filed Sep. 4, 2020, the entire contents of which are herein incorporated by reference. As illustrated in FIGS. 2B-2D, the microfluidic capture stage 210 may comprise a 24.5×60 mm silicon dioxide substrate 220 with a patterned gold thin film layer 224 bonded to a PDMS structure 222 containing four bifurcating microchannels 226*a*-226*d*. The microfluidic capture stage 210 may include microchannels having herringbone structures formed of the gold film and functional graphene oxide nano sheets may be assembled onto the gold thin film layer. The graphene oxide nano sheets may present high-density anti-EpCAM antibodies on the surface of the substrate through chemical cross-linkers. The graphene oxide nano sheets may include any antibody capture structure that is configured to capture candidate cells with the antibody being immobilized on the graphene oxide sheets and extending from the graphene oxide sheets, as illustrated in the inset illustration of FIG. 9. In embodiments, the candidate cell capturing antibody may include one or more of anti-EpCAM, CD133, EGFR, CD44, or another antibody. In embodiments, the candidate cells may include circulating tumor cells (CTCs), circulating tumor DNA (CTDNA), nucleic acids, viral particles, or bacterial particles. In embodiments, opposing outer walls of the herringbone capture channels may be formed of PDMS.

Examples herein are described for in vivo applications to continuously harvest large quantities of candidate cells, such as CTCs. Beyond CTCs, as noted herein, the present techniques may be implemented on any number of target candidate circulating cells or molecules. These candidates include circulating tumor DNA (CTDNA), nucleic acids, viral particles, or bacterial particles. Candidates may include a cancer cell including malignant or benign circulating epithelial cells, endothelial cells, neurons, hepatocytes, nephrons, glial cells, muscle cells, skin cells, adipcytes, fibroblasts, chondrocytes, osteocytes, or osteoblasts. Candidate cells may include immune cells such as Natural Killer cells (NK cells), T cells, B cells and other Lymphocytes, macrophages. Candidates may include a cell expression including a marker of any of prostate cancer, lung cancer, adenocarcinoma, adenoma, adrenal cancer, basal cell carcinoma, bone cancer, brain cancer, breast cancer, bronchi cancer, cervical dysplasia, colon cancer, epidermoid carcinoma, Ewing's sarcoma, gallbladder cancer, gallstone tumor, giant cell tumor, glioblastoma multiforma, head cancer, hyperplasia, hyperplastic corneal nerve tumor, in situ carcinoma, intestinal ganglioneuroma, islet cell tumor, Kaposi's sarcoma, kidney cancer, larynx cancer, leiomyoma tumor, liver cancer, malignant carcinoid, malignant hypercalcemia, malignant melanomas, marfanoid habitus tumor, medullary carcinoma, metastatic skin carcinoma, mucosal neuromas, mycosis fungoide, neck cancer, neural tissue cancer, neuroblastoma, osteogenic sarcoma, osteosarcoma, ovarian tumor, pancreas cancer, parathyroid cancer, pheochromocytoma, primary brain tumor, rectum cancer, renal cell tumor, retinoblastoma, rhabdomyosarcoma, seminoma, skin cancer, small-cell lung tumor, soft tissue sarcoma, squamous cell carcinoma, stomach cancer, thyroid cancer, topical skin lesion, veticulum cell sarcoma, or Wilm's tumor. Circulating tumor DNA (ctDNA), i.e., DNA captured from cancer cells and tumors, may be found in the blood, for example, after cells are broken down. The techniques herein may thus be implemented using CTDNA compatible DNA affinity probes (e.g., DNA hybridization) to capture CTDNA in a carrier fluid, such as blood Like CTC capture, capture of these other candidates can be used to reliably detect cancer and monitor tumor dynamics.

The devices herein may be deployed in a portable form factor to allow patients to carry or wear them with them throughout normal physical activity. In some examples, the devices are deployed in a wearable form factor, for example, where the housing of the capturing circulating tumor cells (or other target capture cells or molecules) device is mounted in a wearable structure that allows for releasable attaching to a patient. Such wearable structures include a removable band structure for attaching to an arm or leg of a patient or a removable patch structure for attaching to any number of locations on the body through a releasable adhesive.

Figure 10:
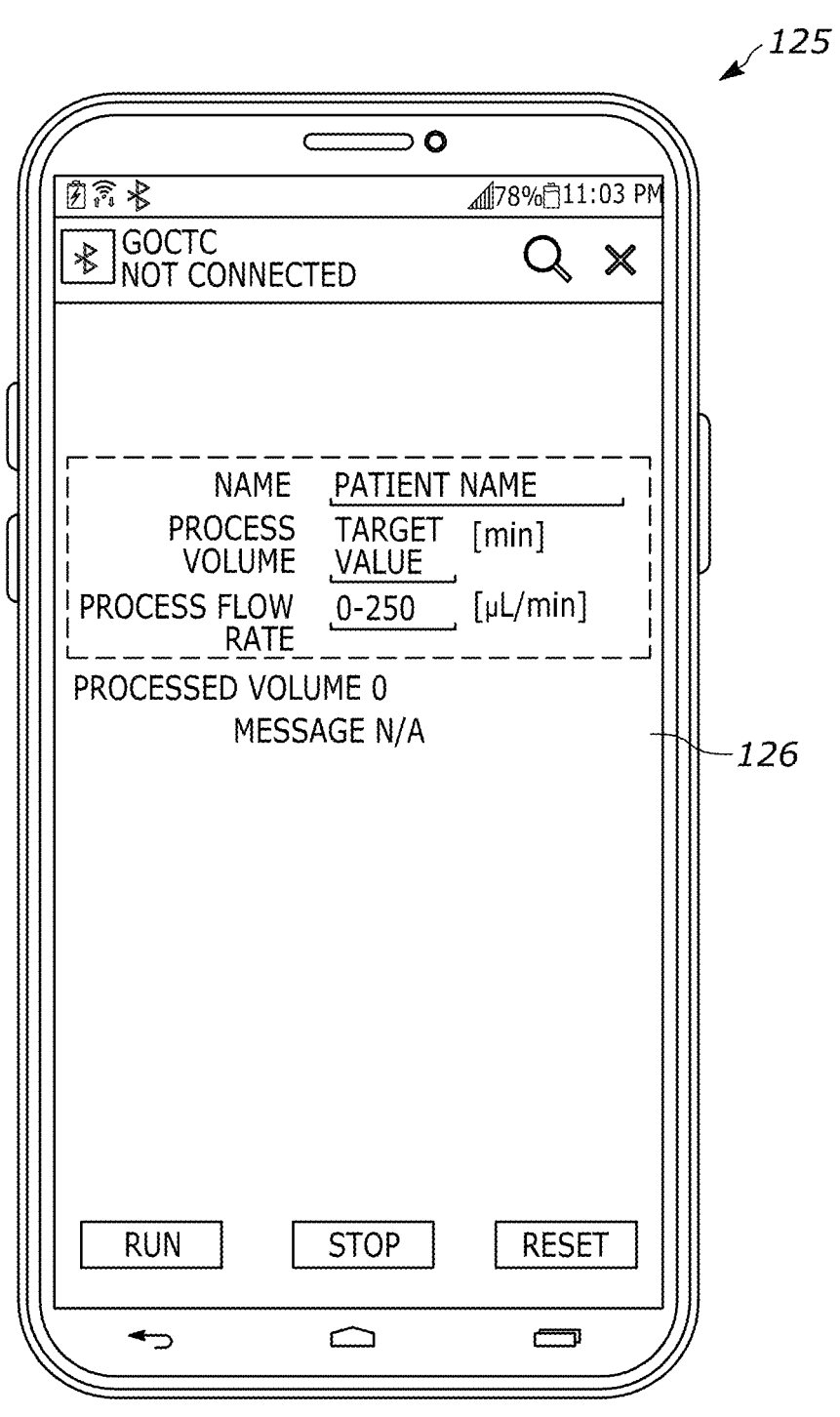
FIG. 10 is a schematic illustration of an example of a display provided by a user interface of a controller for controlling a system for performing in vivo detection of CTCs, in accordance with an example.

In embodiments, such as the embodiment of the system 100 of FIGS. 1A-1C, the controller 125 may control one or more operations of the system 100. For example, the controller 125 may be a portable device having a display screen and the controller may include a memory that stores machine readable instructions. The machine readable instructions may cause the controller 125 to display a user interface for a user to interact with for the user to provide commands to the system 100 by way of the controller 125. FIG. 10 is a schematic illustration of an example of a display provided by a user interface 126 of the controller 125. As illustrated in FIG. 10, the display screen may include fields for entering information such as a patient name, a desired amount of blood to process (i.e., process volume), a process flow rate, etc. Further, the interface 126 may provide to a user an option to run the system 100 according to the input parameters, and the interface 126 may provide the user an option to stop operation of the system 100. In embodiments, a user may use the stop function to pause operation of the system 100, or the interface may provide a user with a separate option to pause the operation of the system 100. The interface 126 may provide the user with an option to reset the parameters which may reset the processed volume to zero, clear error messages, and/or turn off the system 100 for the user to change out a chip of the system 100, or for the user to perform other maintenance of the system 100 or other physical operations. In embodiments, the controller 125 may store record data pertaining to a patient such as process volume for a given period of operation of the system 100, flow rate for a given operation of the system 100, number of sessions of operation of the system 100, total blood volume analyzed, number of CTCs detected, name of a patient, blood oxygen level, errors of the system 100, and other information indicative of operation of the system 100 and/or of the patient. In embodiments, the controller is configured to provide data to another computer or network to store data and/or provide data with another user or individual (e.g., a doctor or physician). In embodiments, the data may be provided by the controller to another computer or individual for further analysis of the data.

In embodiments, the controller 125 includes a communication module with the communication module being able to communicate with the system 100. The communication module may include a Bluetooth module that communicates with the system 100 to control the system. In embodiments, the communication module may include one or more communication chips or devices configurable to communicate with the system 100 via any suitable communication means, including wired and/or wireless connectivity components that implement one or more communication protocol standards like, for example, TCP/IP, WiFi (802.11b), Bluetooth, Ethernet, or any other suitable communication protocols or standards.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a non-transitory, machine-readable medium) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by size, space, cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

What is claimed is:

1. A device for capturing circulating candidate cells from blood, the device comprising:

a housing having a fluid inlet channel to receive the blood from the vasculature of a subject and a fluid outlet channel to return the blood to the vasculature;

a peristaltic pump module encapsulated within the housing and fluidly coupled to the inlet channel to receive the blood at a first flow rate and to convert to a second flow rate and output the blood from a pump outlet channel at the second flow rate;

a candidate cell capture module within the housing and having a microfluidic capture stage to capture the circulating candidate cells with the blood from the vasculature before providing the return of the blood to the vasculature; and a control system to control operating characteristics of the peristaltic pump module, the control system having a pressure sensor to measure continuous pressure fluctuations of the peristaltic pump module and a feedback control configuration to adjust the operating characteristics of the peristaltic pump module in response to the measured continuous pressure fluctuations, wherein the control system is configured to compare the continuous pressure fluctuations from the pressure sensor to a reference pressure corresponding to the peristaltic pump module and from the comparison determine a change in the operating characteristics of the peristaltic pump module.

2. The device of claim 1, wherein the pressure sensor is positioned to measure the continuous pressure fluctuations at an output end of the peristaltic pump module.

3. The device of claim 1, wherein the pressure sensor is positioned to measure the continuous pressure fluctuations at an interim position of the peristaltic pump module proximal to an output end of the peristaltic pump module.

4. The device of claim 1, wherein the reference pressure corresponds to an input end of the peristaltic pump module.

5. The device of claim 4, wherein the control system is configured to determine the change in the operating characteristics by applying the comparison of the continuous pressure fluctuations to the reference pressure to a predicted flow rate versus pressure model of the control system.

6. The device of claim 4, wherein the continuous pressure fluctuations comprise pressure frequency, pressure amplitude, and/or pressure waveform fluctuation.

7. The device of claim 6, wherein the pressure sensor is to measure the pressure frequency, pressure amplitude, and/or pressure waveform fluctuation after fluid has passed through a fluidic resistor at an output end of the peristaltic pump module.

8. The device of claim 1, wherein the control system is configured as a proportional-integral-derivative (PID) control system.

9. The device of claim 1, wherein the feedback control configuration is to adjust the operating characteristics of the peristaltic pump module in response to the measured continuous pressure fluctuations by adjusting a periodic voltage signal to the peristaltic pump module to reduce subsequent measured continuous pressure fluctuations.

10. The device of claim 9, wherein the feedback control configuration is to adjust the operating characteristics of the peristaltic pump module in response to the measured continuous pressure fluctuations by adjusting a periodic voltage signal to the peristaltic pump module to reduce fluctuations in pressure frequency, pressure amplitude, and/or pressure waveform.

11. The device of claim 1, wherein the microfluidic capture stage comprises a plurality of the herringbone grooved capture channels each in parallel to one another.

12. The device of claim 11, wherein each of the herringbone grooved capture channels are formed of a silicon dioxide substrate patterned with a gold film to form the herringbone grooved capture channels.

13. The device of claim 12, wherein opposing outer walls of the herringbone grooved capture channels are formed of polydimethylsiloxane (PDMS).

14. The device of claim 1, wherein the circulating candidate cells are circulating cancer cells.

15. The device of claim 14, wherein the circulating candidate cells are circulating tumor cells (CTC), circulating tumor DNA (CTDNA), nucleic acids, viral particles, or bacterial particles.

16. The device of claim 1, wherein the circulating candidate cells are malignant circulating epithelial cells, benign circulating epithelial cells, endothelial cells, neurons, hepatocytes, nephrons, glial cells, muscle cells, skin cells, adipcytes, fibroblasts, chondrocytes, osteocytes, or osteoblasts.

17. The device of claim 1, wherein the circulating candidate cells are Natural Killer cells (NK cells), T cells, B cells or other Lymphocytes, or macrophages.

18. The device of claim 1, where the circulating candidate cells express at least one marker of prostate cancer, lung cancer, adenocarcinoma, adenoma, adrenal cancer, basal cell carcinoma, bone cancer, brain cancer, breast cancer, bronchi cancer, cervical dysplasia, colon cancer, epidermoid carcinoma, Ewing's sarcoma, gallbladder cancer, gallstone tumor, giant cell tumor, glioblastoma multiforma, head cancer, hyperplasia, hyperplastic corneal nerve tumor, in situ carcinoma, intestinal ganglioneuroma, islet cell tumor, Kaposi's sarcoma, kidney cancer, larynx cancer, leiomyoma tumor, liver cancer, malignant carcinoid, malignant hypercalcemia, malignant melanomas, marfanoid habitus tumor, medullary carcinoma, metastatic skin carcinoma, mucosal neuromas, mycosis fungoide, neck cancer, neural tissue cancer, neuroblastoma, osteogenic sarcoma, osteosarcoma, ovarian tumor, pancreas cancer, parathyroid cancer, pheochromocytoma, primary brain tumor, rectum cancer, renal cell tumor, retinoblastoma, rhabdomyosarcoma, seminoma, skin cancer, small-cell lung tumor, soft tissue sarcoma, squamous cell carcinoma, stomach cancer, thyroid cancer, topical skin lesion, veticulum cell sarcoma, or Wilm's tumor.

19. The device of claim 1, wherein the housing is attached to a wearable mount for releasably attaching the housing to an exterior of a patient.

20. The device of claim 1, wherein the reference pressure corresponds to a desired flow rate, $q_r$.

* * * * *